United States Patent [19]

Rousseau

[11] Patent Number: 5,971,995
[45] Date of Patent: Oct. 26, 1999

[54] SURGICAL POUCH INSTRUMENT

[75] Inventor: Robert A. Rousseau, Ottsville, Pa.

[73] Assignee: Ethicon, Inc., Somerville, N.J.

[21] Appl. No.: 09/050,300

[22] Filed: Mar. 30, 1998

[51] Int. Cl.$^6$ .............................. A61B 17/24; A61B 17/26
[52] U.S. Cl. ............................................. 606/114; 606/110
[58] Field of Search .................................... 606/114, 115, 606/110

[56] References Cited

U.S. PATENT DOCUMENTS

| | | |
|---|---|---|
| 4,557,255 | 12/1985 | Goodman . |
| 4,665,906 | 5/1987 | Jervis . |
| 4,790,812 | 12/1988 | Hawkins, Jr. et al. . |
| 4,997,435 | 3/1991 | Demeter . |
| 5,037,379 | 8/1991 | Clayman et al. . |
| 5,074,867 | 12/1991 | Wilk . |
| 5,143,082 | 9/1992 | Kindberg et al. . |
| 5,147,371 | 9/1992 | Washington et al. . |
| 5,176,687 | 1/1993 | Hasson et al. . |
| 5,190,542 | 3/1993 | Nakao et al. . |
| 5,190,555 | 3/1993 | Wetter et al. . |
| 5,192,284 | 3/1993 | Pleatman . |
| 5,192,286 | 3/1993 | Phan et al. . |
| 5,201,740 | 4/1993 | Nakao et al. . |
| 5,215,521 | 6/1993 | Cochran et al. . |
| 5,234,439 | 8/1993 | Wilk et al. . |
| 5,279,539 | 1/1994 | Bohan et al. . |
| 5,308,327 | 5/1994 | Heaven et al. . |
| 5,312,416 | 5/1994 | Spaeth et al. . |
| 5,330,483 | 7/1994 | Heaven et al. . |
| 5,336,227 | 8/1994 | Nakao et al. . |
| 5,337,754 | 8/1994 | Heaven et al. . |
| 5,341,815 | 8/1994 | Cofone et al. . |
| 5,352,184 | 10/1994 | Goldberg et al. . |
| 5,352,219 | 10/1994 | Reddy . |
| 5,354,303 | 10/1994 | Spaeth et al. ............................ 606/114 |
| 5,368,597 | 11/1994 | Pagedas . |
| 5,374,273 | 12/1994 | Nakao et al. . |
| 5,417,697 | 5/1995 | Wilk et al. . |
| 5,465,731 | 11/1995 | Bell et al. . |
| 5,480,404 | 1/1996 | Kammerer et al. . |
| 5,486,182 | 1/1996 | Nakao et al. . |
| 5,486,183 | 1/1996 | Middleman et al. . |
| 5,499,988 | 3/1996 | Espiner et al. . |
| 5,524,633 | 6/1996 | Heaven et al. . |
| 5,535,759 | 7/1996 | Wilk . |
| 5,554,151 | 9/1996 | Hinchliffe . |
| 5,611,803 | 3/1997 | Heaven et al. . |
| 5,630,822 | 5/1997 | Hermann et al. . |
| 5,632,746 | 5/1997 | Middleman et al. . |
| 5,647,372 | 7/1997 | Tovey et al. . |
| 5,681,324 | 10/1997 | Kammerer et al. . |

Primary Examiner—Michael Buiz
Assistant Examiner—Vy Q. Bui

[57] ABSTRACT

A surgical pouch instrument has three elongated coaxial members, each capable of telescopic movement relative to the others. A surgical pouch is supported upon a plurality of support blades attached to a distal end of the innermost coaxial member. The pouch support blades having a deployed configuration approximating a hoop which is mechanically discontinuous at one point with the discontinuity compensated for by the overlapping of the blades. In a stored configuration, at least one of the blades is folded back upon another to permit the hoop to be compressed for storage without extending to its full compressed length. A preferred embodiment features an independent blade that overlaps and bridges the gap between two blades that are attached to the innermost member.

27 Claims, 6 Drawing Sheets

SURGICAL POUCH INSTRUMENT

FIELD OF THE INVENTION

The present invention relates to a surgical instrument for receiving, retaining and removing matter from a surgical site used in the course of minimally invasive surgery for introducing, positioning, opening and sealably closing a pouch for containing the matter to be removed.

BACKGROUND OF THE INVENTION

Endoscopic surgery has become popular and commonplace for certain surgical procedures, such as gall bladder removal, ovariectomies and for appendectomies. In such procedures, diseased, malignant, necrotic or inflamed tissues and/or organs are excised and removed from the patient. Similarly, adhesions, gall and kidney stones, polyps and tumors may be removed using endoscopic surgical techniques. In many of the foregoing procedures, a bag or pouch is used to contain the matter to be removed from the patient's body. The purpose of the pouch is to contain and isolate the infected or irritating matter upon its separation from the patient's internal organs such that it is not lost at the internal surgical site, e.g., the abdominal cavity, and/or does not infect or irritate healthy organs with which it might otherwise come in contact. Surgical pouches also provide a mechanism for firmly grasping the excised matter. Since the pouches are most commonly formed of a resilient, fluid impenetrable polymer film, liquids and flowable exudate may be contained within the pouches which typically have a noose, constricting band or other means for sealing the mouth of the pouch.

DESCRIPTION OF THE RELATED ART

Various apparatus have been devised for introducing opening, positioning and closing surgical pouches and for removing the pouches and enclosed matter from the surgical site. For example, in U.S. Pat. Nos. 5,465,731 to Bell et al. and 5,647,372 to Tovey et al., a specimen retrieval pouch is supported by a loop composed of two approximately semi-circular, metallic portions joined at their distal ends by a length of polymer shrink-wrap tubing. The metallic portions are preferably composed of a highly flexible material, such as stainless steel or super elastic metal. The pouch has a noose retained proximate its open end and is perforated proximate its attachment to the support loop. The pouch support loop is mounted upon one end of a rod that is slidably received within the bore of an outer tube. The rod and the tube have handles affixed to their proximal ends to facilitate relative telescopic movement. When in its retracted position within the tube, the loop and its attached pouch are housed within the distal hollow end of the outer tube. In order to fit within the outer tube, the rounded semi-circles of the loop flatten and the shrink wrap tubing folds. After the pouch receives its intended contents at the surgical site, it is cinched closed by pulling upon a suture leading to the noose. A slip knot in the suture encounters the periphery of a small hole in a top surface of the loop rod, thus tightening the noose. A pull ring is provided at the proximal end of the suture to aid in this process. Cinching the pouch closed aids the separation of the pouch from the support loop via tearing along the perforation line. Once the pouch has been torn from the expanded loop pouch support, the support may be retracted back into its shielded position within the hollow of the outer tube to facilitate withdrawal of the instrument from the cannula port.

Whereas the foregoing patents represent apparatus for using surgical pouches during endoscopic surgery, there remains a need for alternative designs which feature improved ergonomics, e.g., relating to the length of the "stroke" or displacement required to be executed by the hand of the surgeon to deploy the surgical pouch. As can be appreciated, e.g., in the disclosure of U.S. Pat. No. 5,465,731, the stroke required to deploy the support loop for the surgical pouch is at least as long as the flattened length of the support loop.

It also remains an objective to produce an endoscopic pouch wherein the pouch is readily detachable from the support rim while maintaining rigidity of the rim to provide adequate rim support, and further, to have a pouch that does not impede retraction by, e.g., becoming bound in or pinched between retracting parts. In designing surgical instruments, it is an ever-present objective to design same such that they are prevented to the maximum extent possible from being used incorrectly through inadvertence or error. With respect to surgical pouch handling apparatus, it would be desirable for assurances to be provided that guarded against inappropriate deployment of the surgical pouch, the improper orientation of the device at various stages of use and/or the inadvertent failure to seal a specimen within the pouch leading to the escape of specimen contents.

BRIEF SUMMARY OF THE INVENTION

The problems and disadvantages associated with the conventional techniques and devices utilized to position, deploy and close a surgical pouch are overcome by the present invention which includes a surgical instrument with an elongated outer tube and an elongated inner rod telescopically moveable within the outer tube. A plurality of pouch support blades are attached to a distal end of the inner rod for supporting a pouch having an open end and a closed end. The support blades are accommodated in a blade channel in the pouch extending at least partially around and proximate to the periphery of the open end. The blades have a deployed configuration approximating a hoop with one of the plurality of blades overlapping a portion of a second of the plurality of blades.

BRIEF DESCRIPTION OF THE SEVERAL VIEWS OF THE DRAWINGS

For a better understanding of the present invention, reference is made to the following detailed description of an exemplary embodiment considered in conjunction with the accompanying drawings, in which:

FIGS. 3a and 3b through 5a and 5b and FIG. 14 are diagrammatic, top views of three alternative pouch support blade assemblies in folded and deployed states, respectively;

DETAILED DESCRIPTION OF THE INVENTION

Figure 1:
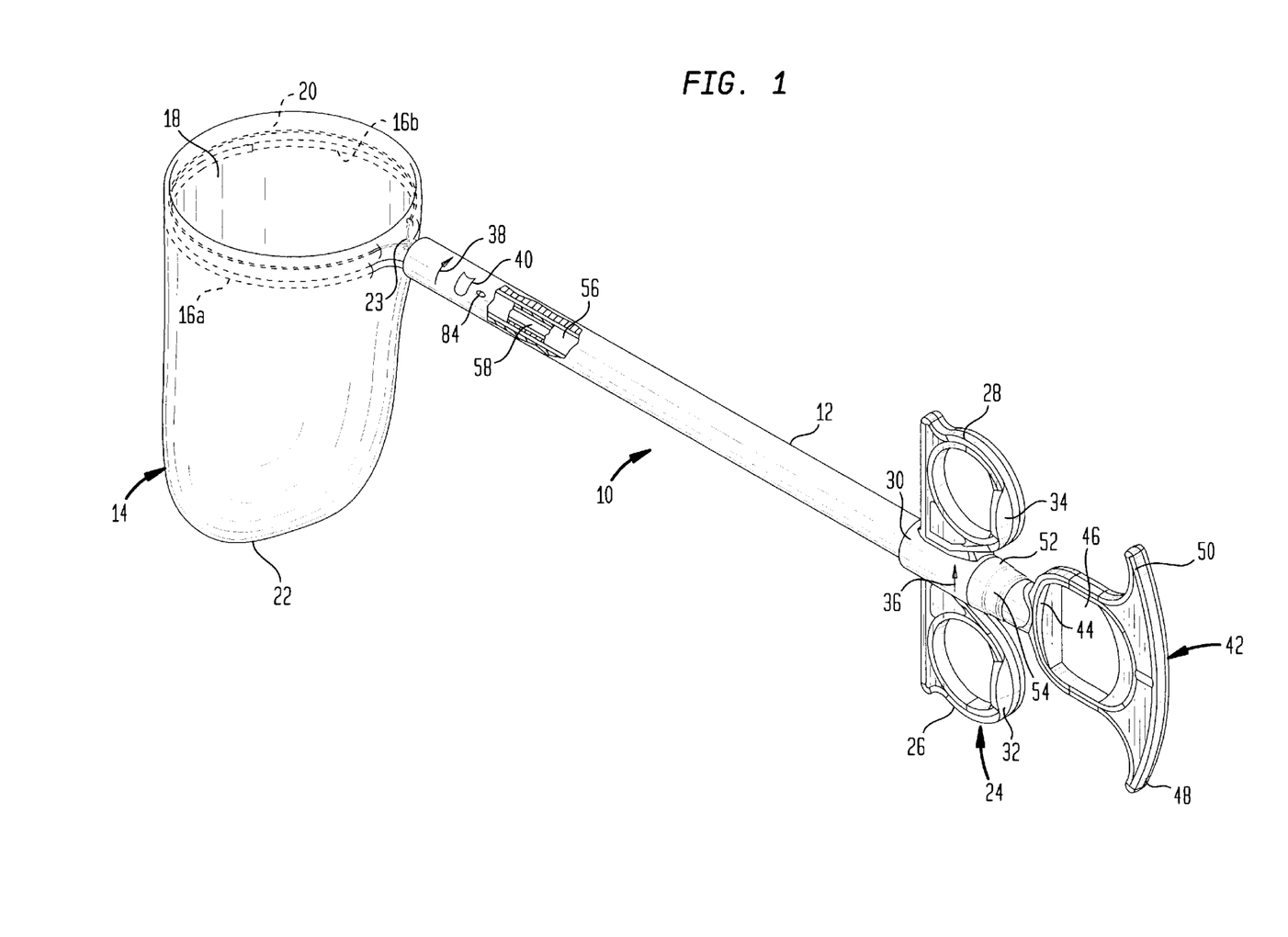
FIG. 1 is a perspective view of a surgical pouch instrument in accordance an embodiment of the present invention.

FIG. 1 shows a surgical pouch instrument 10 of the present invention having an elongated introducer tube 12 with a surgical pouch 14 deployed at a distal end thereof. Throughout the remainder of this specification "distal" and "proximal" shall be defined relative to the surgeon that uses the instrument. The pouch 14 is supported upon pouch support blades 16a, 16b which have a variety of configurations in accordance with alternative embodiments of the present invention as described below. The support blades 16a, 16b are slip-fitted within a hollow channel or lumen provided in the periphery of the upper, open end 18 of the pouch 14. The pouch 14 open end 18 also incorporates a cinching suture 20 threaded about the periphery thereof, i.e., within an associated peripheral channel provided in the pouch. A closed end 22 contains matter to be removed. The pouch 14 is preferably formed from polyurethane or any other tough, flexible, biocompatible material that is sufficiently supple to allow it to be flattened and rolled into a tight roll or "cigar" to facilitate loading the pouch 14 into the introducer tube 12 for storage prior to deployment. A non-reversible slip knot 23, such as described in U.S. Pat. No. 5,279,539 to Bohan et al. And U.S. Pat. No. 5,143,082 to Kindberg et al., which are incorporated herein by reference for their teachings in that regard, forms the distal end of the suture 20 into a noose for closing the pouch 14. The proximal end of the suture 20 threads through the elongated portion of the instrument 10 to allow the surgeon to constrict the pouch opening 18 from the proximal end of the instrument 10, as shall be further described below.

A grip 24 having a pair of finger loops 26, 28 extending from a central barrel section 30 is affixed at the proximal end of the introducer tube 12. In the embodiment shown FIG. 1, the finger loops 26, 28 extend at 90 degrees relative to the blades 16a, 16b, however, any angular orientation can be used in accordance with the present invention. Each of the finger loops 26, 28 may be provided with a tactile orientation indicator 32, 34 extending from their surface to provide a tactile signal to the hand of the surgeon indicating the orientation of the device 10. To preserve symmetry and universality of presentation for use by left and right handed surgeons, the tactile orientation indicators 32, 34 may be omitted or greatly reduced in size. This is particularly applicable to embodiments of the present invention wherein the grip 24 is at an orientation as shown in FIG. 1. Other orientation indicators may be provided including graphical indicator 36 on the barrel of the syringe grip 24 and graphical indicators 38, 40 on the distal and proximal ends of the introducer tube 12. The indicators 36 and 38 are arrows pointing in the upward direction, while indicator 40 shows the opened shape of the pouch 14. The indicators 38, 40 are intended to be utilized by visualization through a laparoscope directed at the surgical site during endoscopic surgery, i.e., when the instrument 10 is extended within the patient.

The surgical instrument 10 includes a thumb ring 42 to facilitate actuation of the device and which may incorporate a tactile orientation indicator 44 similar to those provided on the syringe grip 24. The thumb ring 42 has a central aperture 46 for receiving the thumb of the surgeon, and a pair of opposing extensions 48, 50 which are curved to receive the fingers of a surgeon for pulling the thumb ring 42 in a proximal direction. A syringe grip end cap 52 and a pusher tube proximal end cap 54 serve as motion limiters that constrain the motion of the moveable components of the instrument 10, as shall be described below.

The instrument 10 includes three substantially coaxial, elongated members which move telescopically relative to each other. Specifically, a hollow pusher tube 56 is disposed within the lumen of the introducer tube 12. The pusher tube 56 accommodates within its lumen a push/pull rod 58. Each of the elongated elements must be sufficiently mechanically strong to effectively withstand the stress of surgery and provide a wide margin of safety against breakage. The instrument 10 is preferably made from conventional biocompatible materials. For example, the introducer tube 12 is preferably made from stainless steel, the pusher tube 56 and push/pull rod 58 are preferably formed from polycarbonate and liquid crystal polymer or other resilient polymer.

Figure 2:
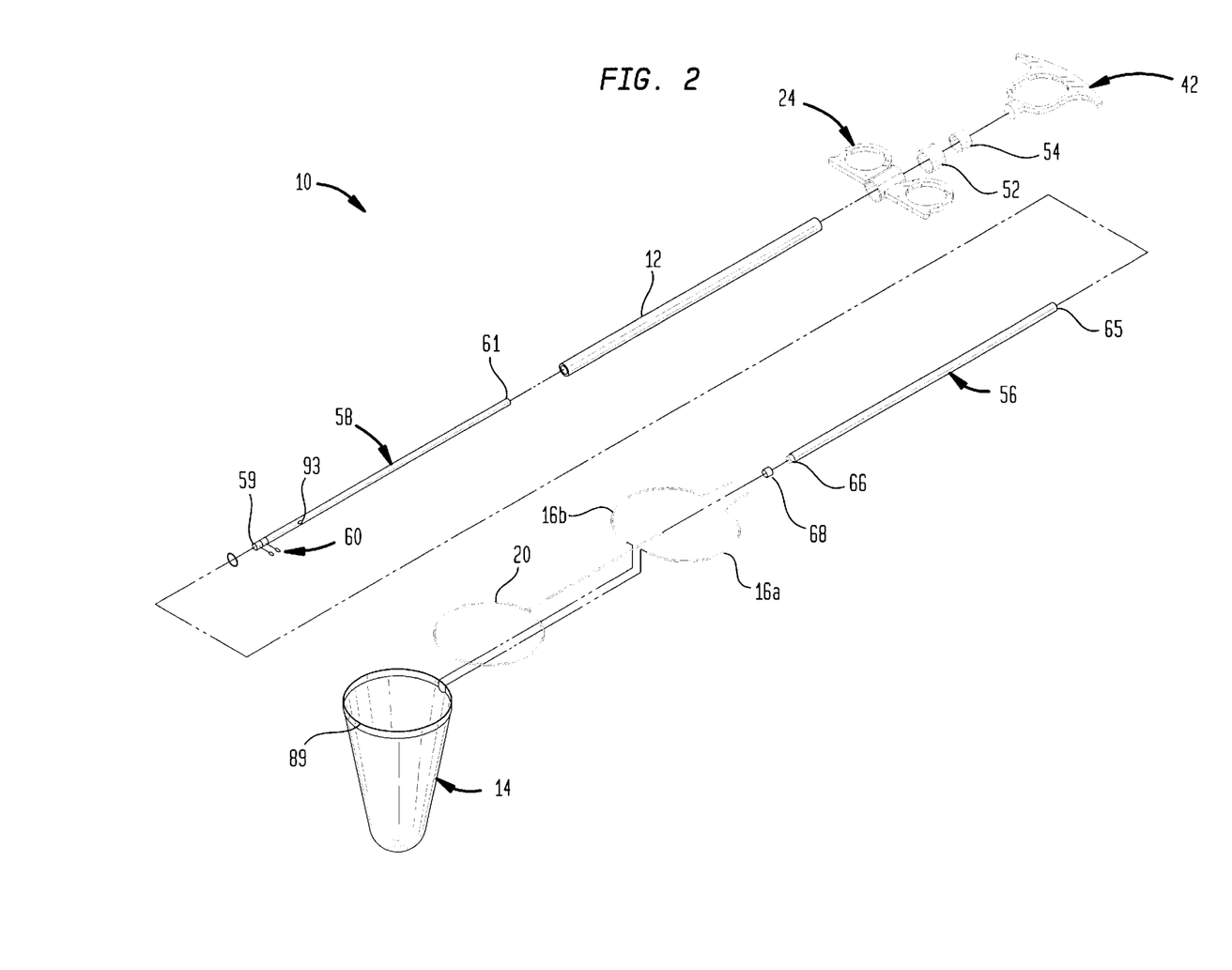
FIG. 2 is an exploded view of the instrument of FIG. 1.

Referring now to FIG. 2, the support blades 16a, 16b attach to the push/pull rod 58 at the distal end 59 via pins or rivets 60 or other conventional means such as plastic welding or deformation to embed the blades 16a, 16b in the rod 58. To maintain correct relative alignment of the blades 16a, 16b, they may be jigged and spot welded prior to attachment to the rod 58. The thumb ring 42 is attached at the proximal end 61 of the push/pull rod 58 via glue, pinning or other conventional means. A suture channel 57 (See FIG. 6) is provided along the length of the push/pull rod 58 to accommodate the cinch suture 20 such that the suture 20 can internally pass from the distal end of the instrument 10 to the proximal end without disturbing the close coaxial telescoping relationship between the push/pull rod 58, pusher tube 56 and introducer tube 12. A flat 62 (see FIG. 8) may be provided at the proximal end 61 of the push/pull rod 58 to facilitate cutting the suture 20 after the pouch has been cinched shut as described below. A through hole 63 (see FIG. 8) may be provided in the push/pull rod 58 proximate to or in the flat 62 to hold the suture 20 to the push/pull rod by a releasable knot 64.

The distal end 66 of the pusher tube 56 has a reduced diameter for receiving a distal end cap 68 with at least one support blade aperture 70 (see FIG. 10) and a suture aperture 72. The end cap 68 is snap-fitted, glued or plastic welded in a conventional manner to the reduced diameter portion 66. The suture aperture 72 in the distal end cap 68 allows the suture 20 to pass through it but will not allow the slip knot 23 to pass. In a similar manner, the proximal end 65 of the pusher tube 56 retains the proximal end cap 54. The proximal end cap 54 may retain a one-way sliding clamp washer 67 (See FIG. 12) with a plurality of inwardly directed teeth 69 that are bent in the proximal direction. The proximal end cap 54 has a proximal opening 71 allowing the push/pull rod 58 to pass through the end cap 54. When the end cap 54 and clamp washer 67 are in place on the proximal end 65 of the pusher tube 56 and the push/pull rod 58 is inserted into the pusher tube 56 such that it passes through the end cap 54 and the clamp washer 67, the clamp washer teeth 69 permit the push/pull rod 58 to move in a proximal direction but cut into and stop it from moving through the end cap 54 in a distal direction. Alternatively, the clamp washer 67 can be omitted and the inherent misalignment of the retracted blades 16a, 16b, 16c relative to the blade apertures 70, 70a, 70b (See FIGS. 10 and 11) relied upon to prevent redeployment of the blades 16a, 16b, 16c. More particularly, when the blades 16a, 16b, 16c are retracted into the pusher tube 56 they tend to expand and press against the pusher tube 56 causing them to be out of alignment with the apertures 70a, 70b in the end cap 68 such that the blades 16a, 16b, 16c will not redeploy through the end cap 68.

The pusher tube 56 has an elongated flat 73 (see FIG. 6) formed along a portion of its length. The flat 73 acts as a range of motion limiter in that it controls the extent that the pusher tube 56 can extend in the proximal direction and also limits its rotational motion. This is accomplished through interaction with the grip 24 and grip end cap 52, which, similar to the pusher tube end cap 54, captures a one way clamp washer 75(see FIG. 7), but with teeth that point in the distal direction, such that the pusher tube 56 can be passed through the clamp washer in a distal direction but can not pass in an opposite direction. The grip end cap 52, like the pusher tube end cap 54 has an opening (not shown) therein through which the pusher tube 56 may pass. The opening in the syringe grip end cap 52 is "D" shaped such that it is complementary to the cross-section of the pusher tube 56 in the area of the flat 73.

Figure 3A:
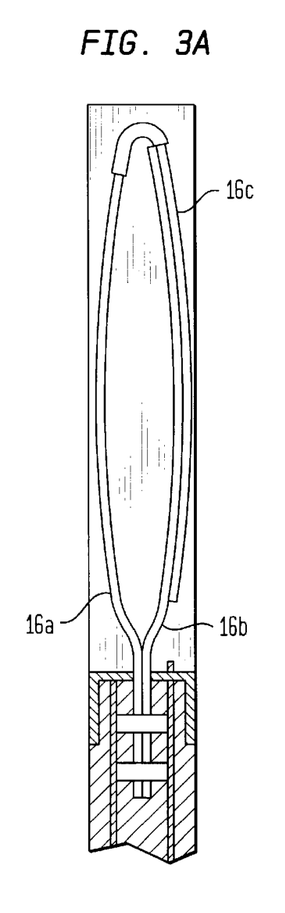
Figure 3B:
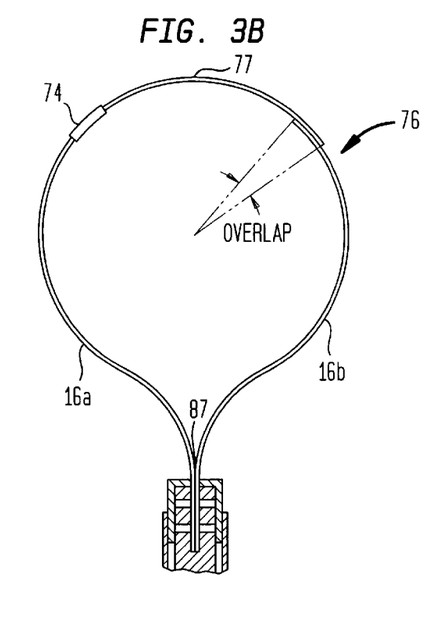

As shown in FIGS. 3*a* and 3*b*, the support blades 16*a*, 16*b*, and 16*c* of a first embodiment of the present invention are three in number. The two longer support blades 16*a* and 16*b* are both substantially smaller than a pair of mirror image blades that when assembled to a mounting would join at their respective tips when deployed to approximate a continuous loop with a split at the distal apex 77(see FIG. 3*b*). Instead, the present invention utilizes a bridge blade 16*c* to complete the pouch support loop, i.e., to bridge the gap between the ends of support blades 16*a* and 16*b*. A small segment of highly flexible, tough tubing 74 is used to join support blade 16*a* to blade 16*c* although other means may be utilized, including mechanical formed hinges.

Figure 13:
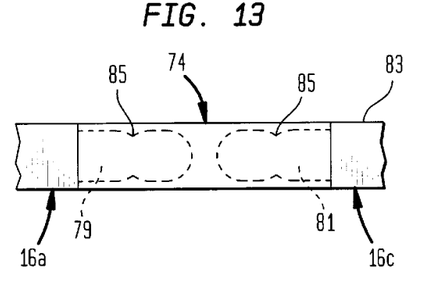
FIG. 13 is an enlarged, partially phantom view of a junction of two pouch support blades in accordance with the embodiment of the invention shown in FIGS. 3a and 3b.

FIG. 13 illustrates the ends 79,81 of the support blades 16*a* and 16*c* that are joined by the tubing 74 are preferably shaped to increase the grip that the tubing 74 has thereon and to avoid any roughness associated with an edge of the tubing 74 extending above the surface 83 of the support blades 16*a*, 16*c*. This can be accomplished by crushing a length of the ends of the blades 16*a*, 16*c* to an extent approximating the thickness of the tubing 74. To increase the grip that the tubing 74 exerts on the blades 16*a* and 16*c*, the ends of the blades can include small radii 85 proximate their tips. The ends 79,81 of the blades 16*a* 16*c* are also rounded to promote insertion into the tube 74. Shrink tubing is particularly suitable for tubing 74, in that it can be readily inserted over the blades 16*a*, 16*c* and then heated to shrink and tightly grasp the blades.

FIG. 3*a* shows that the tubing 74 may be tightly folded, permitting the support blades to assume a compact, folded configuration prior to deployment, with blade 16*c* doubling back over blade 16*b*. Because both blades 16*a* and 16*b* may be made shorter due to the supplementation of length by blade 16*c* when deployed, but which doubles back over blade 16*b*, when folded, the overall folded length of the support blade assembly 76 is significantly smaller than a loop that is simply flattened along a line connecting its distal and proximal apexes, 77, 87. The compact, folded configuration of the assembly 76 has a beneficial ergonomic result in that it shortens the stroke necessary to displace the folded support blades 16*a*, 16*b*, 16*c* from the instrument 10 in order to deploy the surgical pouch 14.

FIG. 3*b* illustrates the support blades 16*a*, 16*b* and 16*c* in their expanded or deployed state. In this expanded state, support blade 16*c* completes a loop 76 by bridging the gap between blades 16*a* and 16*b* with blade 16*c* overlapping blade 16*b*. This overlap provides support against flexure in a direction at right angles to the plane of the loop 76 since the overlapping blades 16*a* and 16*c* are contained closely within the support blade channel 89 of the surgical pouch 14 (see FIG. 2). This arrangement tends to prevent relative flexure of the blades 16*a* and 16*c* out of alignment, in that such flexure would cause the blades 16*a*, 16*c* to bear against the blade channel 89 of the pouch 14.

Figure 4A:
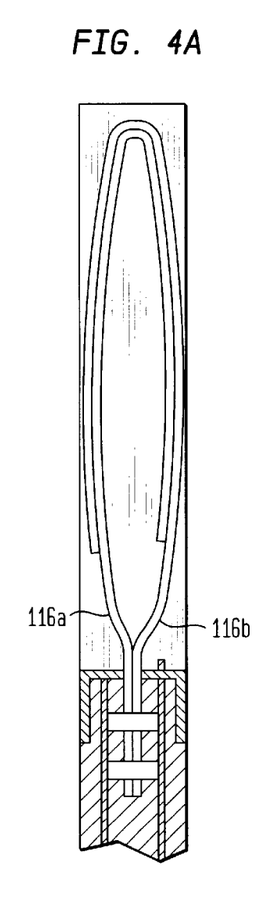
Figure 4B:
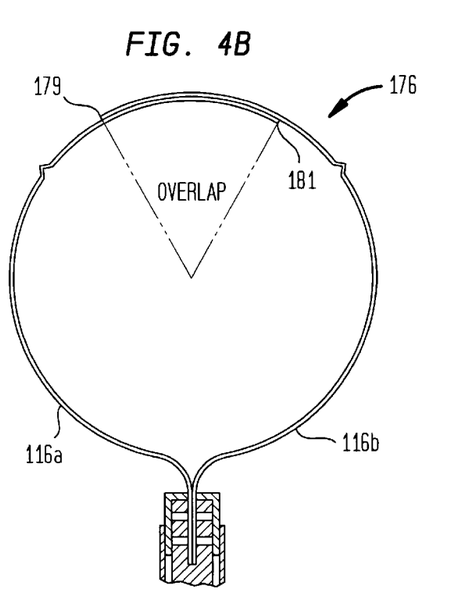

FIGS. 4*a* and 4*b* illustrate another embodiment of the present invention wherein the support blades 116*a*, 116*b* are formed from a superelastic metal, such as Nitinol which is commercially available. Because superelastic metal can withstand being deformed at a severe angle and regain its original shape, the tubing 74 and third support blade 16*c* of the first embodiment can be omitted in favor of lengthened, superelastic blade supports 116*a* and 116*b*. The superelastic metal permits the blades 116*a* and 116*b* to be folded back upon themselves giving the beneficial ergonomic result of shortening the stroke required to deploy the pouch 14. The terminal ends 179, 181 of the support blades 116*a* and 116*b* overlap each other, constraining the terminal ends 179, 181 thereof from becoming misaligned and thereby providing support for the pouch 14.

Figure 5A:
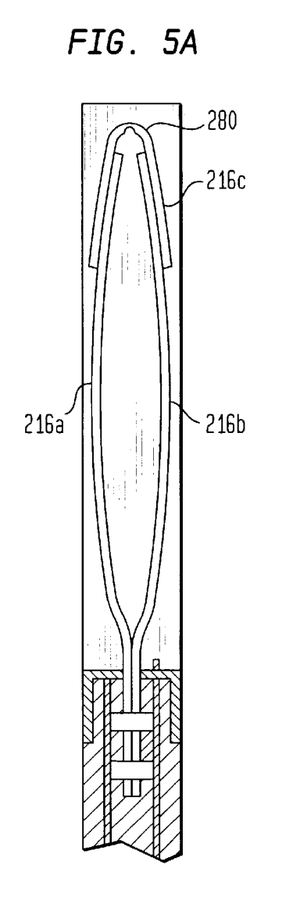
Figure 5B:
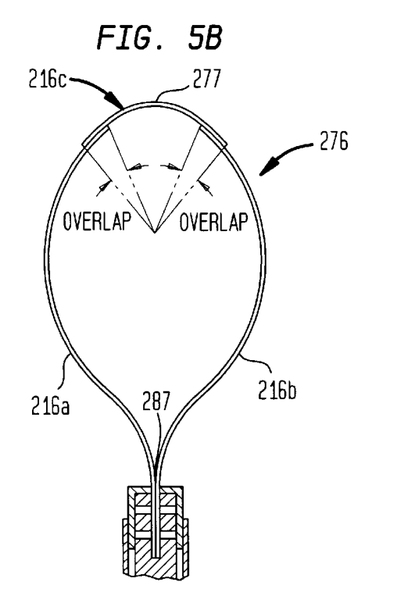

FIGS. 5*a* and 5*b* show yet another embodiment of the present invention wherein a support loop quasi-assembly 276 includes an unattached folding blade 216*c* which is preferably formed from a flexible polymer, such as nylon or PETg. The folding blade 216*c* acts as a bridging blade similar to the blade 16*c* in the first embodiment described above, but is not attached to either blade 216*a* or 216*b*. Instead, the folding blade 216*c* is merely positioned within the support blade channel 89 of the pouch 14 at a position corresponding to the distal apex of the support blade quasi-assembly 276. The blade 216*c* is preferably swaged approximately in the middle to define a hinge point at 280. When the other blades 216*a* and 216*b* are inserted into the blade channel 89 and the pouch 214 is folded along the line joining the distal and proximal apices 277, 287, the folding blade 216*c* folds at flat 280. Once folded, the unattached folding blade 216*c* does not migrate within the blade support channel 89 and an inherent alignment is maintained, i.e., the respective folds at 280 in the blade 216*c* and the pouch 214 remain aligned. Upon deployment, the blades 216*a* and 216*b* flex outward straightening the pouch 214 and the folded blade 216*c*. Since the folded blade 216*c* and the pouch 214 and their relative alignment remain to some degree until complete deployment and because there is a symmetry of forces acting between the pouch 214 and the blades 216*a* and 216*b*, the relative position of the pouch and the folding blade 216*c* is maintained. As shown in the deployed configuration of the support loop quasi-assembly 276 of FIG. 5*b*, there is a significant overlap of blades 216*a* and 216*b* with the folding blade 216*c*. This overlap performs the same stiffening function as the overlap noted above in previously described embodiments of the present invention.

Figure 14:
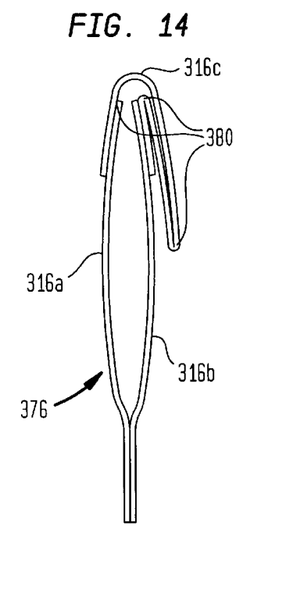

FIG. 14 shows yet another alternative support loop assembly 376 in a folded configuration and having blades 316*a* and 316*b*. A bridge blade 316*c* has three hinge points 380 permitting the blade 316*c* to be folded as shown. In use, the blade assembly 376 would reside in the blade channel 89 of the pouch 14 such that the blade 316*c* would be held in relative juxtaposition to blades 316*a*, 316*b* by the pouch, both when deployed and in the folded condition. A benefit associated with the blade assembly 376 shown in FIG. 14 is that it does not require the sliding of the constituent blades 316*a*,316*b*,316*c* over one another to deploy from the folded condition. Instead, the hinge points 380 straighten upon deployment.

Figure 6:
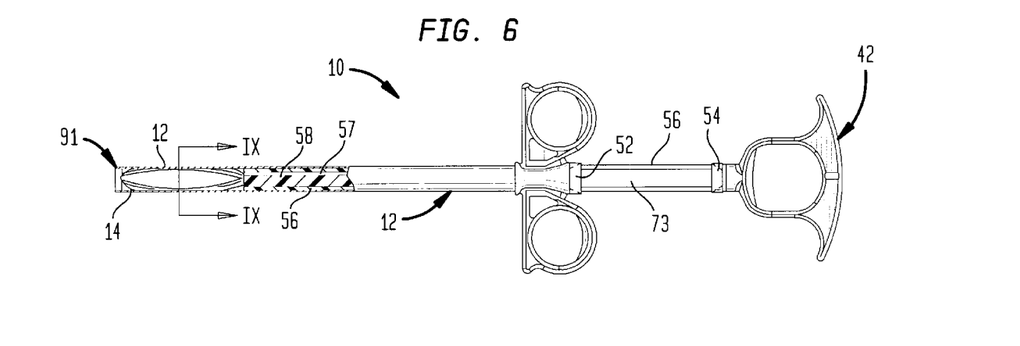
FIGS. 6, 7 and 8 are diagrammatic views of the surgical instrument of the present invention in an undeployed, deployed and retracted state, respectively.

FIG. 6 shows the instrument 10 in the undeployed state with the pusher tube 56 retracted proximally allowing the pouch 14 to reside in the distal end 91 of the introducer tube 12. The push/pull rod 58 is fully home with the thumb ring 42 abutted against the pusher tube end cap 54.

Figure 7:
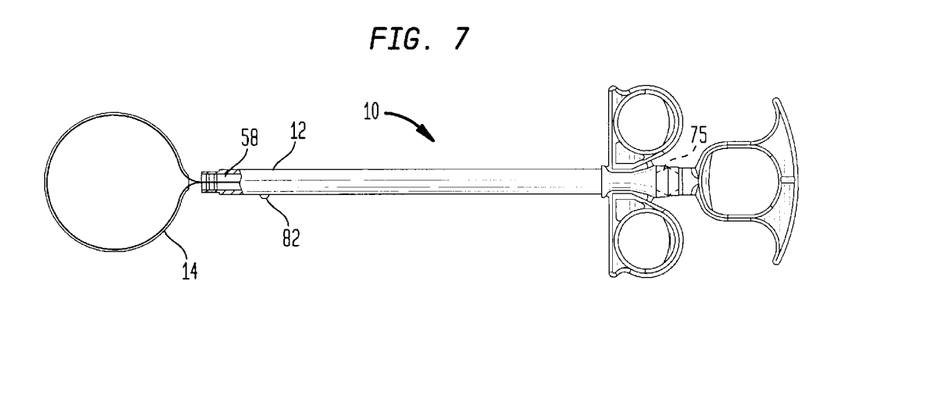

FIG. 7 shows the pouch 14 deployed via full distal insertion of the pusher tube 56 into the introducer tube 12 such that the support blades 16a, 16b, 16c (see FIG. 3b) are free to expand and deploy the pouch. The push/pull rod 58 is still in its fully distal position relative to the pusher tube 56. When the pusher tube 56 is positioned in the deployed position as shown, an interlock pin 82 is free to extend through a relief hole 84 provided in the side of the introducer tube 12 (see FIG. 1) thereby backing out of a lock detent 93 (see FIG.2) provided in the push/pull rod 58. The interlock pin 82 therefore prevents the push/pull rod 58 from being withdrawn proximally prior to the full distal deployment of the pusher tube 56.

Figure 8:
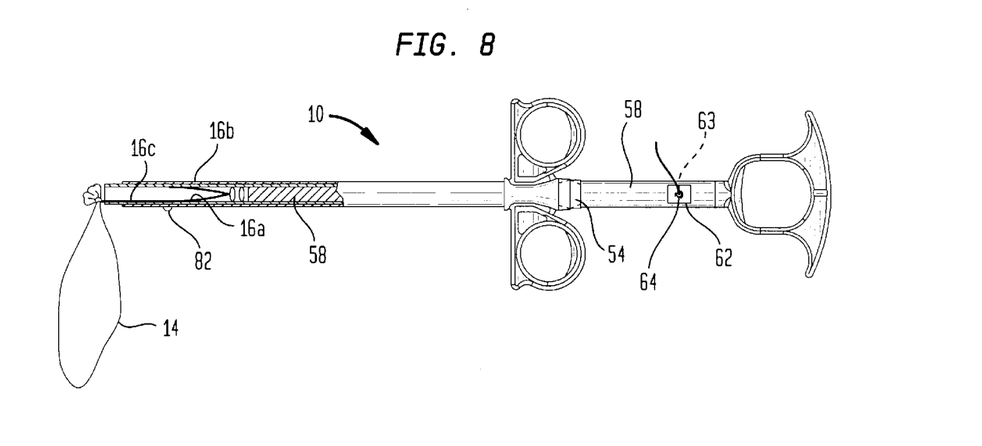

FIG. 8 shows the retracted position of the support blades 16a, 16b, 16c having been drawn back proximally by the retraction of the push/pull rod 58. Upon retraction, the support blades withdraw from the blade channel 89 in the pouch 14 permitting the mouth 18 of the pouch to be cinched closed. The pouch 14 is automatically cinched closed by the slip knot 23 encountering the pusher tubedistal end cap 68 and tightening as the push/pull rod 58 is withdrawn proximally. As noted above, after retraction, either the proximal end cap 54 and enclosed clamp washer 67 and/or the inherent misalignment of the blades 16a, 16b, 16c with the apertures 70a, 70b prevent the push/pull rod 58 from being moved in a distal direction and the blades 16a, 16b, 16c from redeploying.

Figure 9:
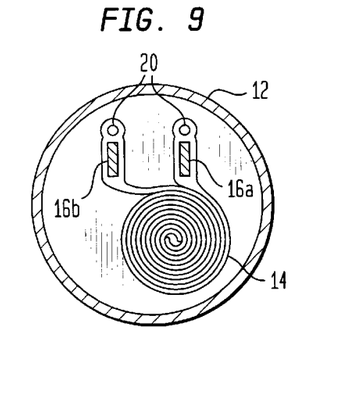
FIG. 9 is a cross-sectional view of the instrument of FIG. 6, taken along line 9—9 and looking in the direction of the arrows.

The position of the rolled pouch 14 within the introducer tube 12 and below the blade supports 16a, 16b is shown in FIG. 9.

Figure 10:
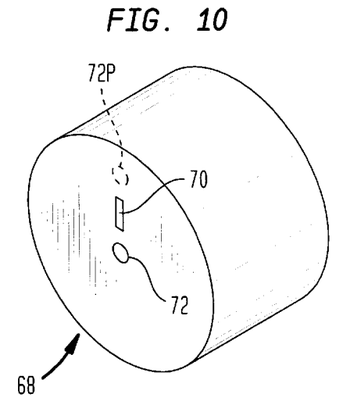
FIGS. 10 and 11 are perspective views of pusher tube end caps in accordance with first and second embodiments of the present invention.

FIG. 10 illustrates a pusher tube distal end cap 68 with one support blade opening 70 which is positioned above the center of the end cap 68 and the suture opening 72. An alternative position for the suture opening 72 is indicated in dotted lines as 72p, which would be utilized for a pouch having the suture 20 located above the channel 89 receiving the support blades 16a, 16b. The purpose of positioning the opening 70 off-center is to allow room for the rolled up pouch 14 to be easily stored in the introducer tube 12 below the support blades 16a, 16b from which it depends. (See FIG. 9).

Figure 11:
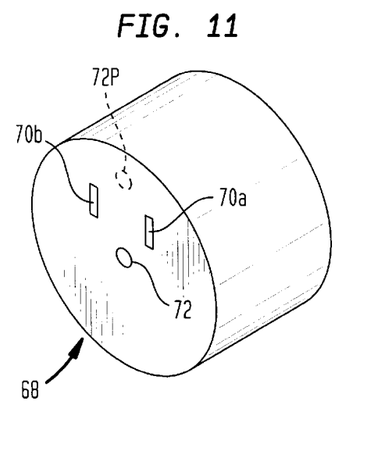
Figure 12:
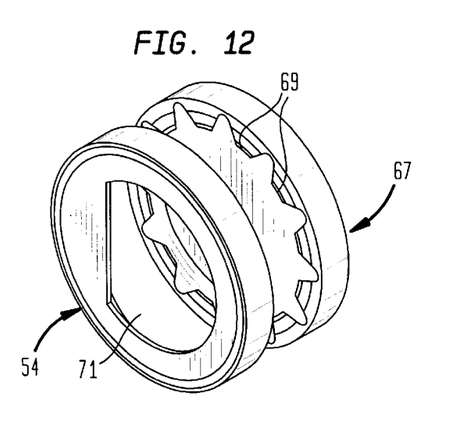
FIG. 12 is an exploded view of a pusher tube end cap and clamp washer as used in an embodiment of the present invention.

FIG. 11 illustrates a pusher tube distal end cap 68 having two support blade openings 70a, 70b above a cinch suture passage 72. The independent openings 70a, 70b prevent the pouch 14 from being pinched between the support blades 16a, 16b when they are retracted. It should be appreciated that the pusher tube end cap 68 could be formed monolithically with the pusher tube 56, rather than be a separate, snap-on element.

The instrument 10 may be packaged in a PETg tray with a Tyvek lid, a support tray loaded inside a Tyvek Mylar envelope, in foil, or other conventional packaging. The instrument 10 may be sterilized by conventional processes including exposure to radiation (Gamma) in its sealed package.

The instrument 10 of the present invention is used in the following manner. After actuation, the suture may be cut or untied from the push/pull rod 58 by pulling on the release knot 64 and the instrument 10 may be removed from the trocar. The suture strand 20 remains attached to the cinched pouch 14 and extends through the trocar. When convenient, the pouch may be pulled through the trocar for removal. The pouch 14 and the trocar may be removed simultaneously through the trocar incision. As a further alternative, the suture may be left attached to the push/pull rod 58 and the instrument 10, trocar and cinched pouch 14 removed together through the trocar incision.

The use of either of the tri-element or the super-elastic pouch support structures 76,176, or 276 in accordance with the present invention decreases the stress required to deform and constrain the support structure 76,176, or 276 resulting in easier loading, a reduction of drag of the pouch 14 against the introducer tube 12, minimizing displacement of the pouch 14 on the support rim 76, 176 or 276 and the potential for damage to the pouch 14. The diminished deformation stress also allows the pouch 14 to be deployed with less actuation force.

Each pouch support embodiment 76, 176 or 276 shown herein exhibits a smaller collapsed length than similarly sized continuous loop supports of the prior art that simply fold flat. This reduction in compressed length allows the pouch 14 to be deployed by a shorter displacement which particularly benefits surgeons with small hands. The nonreversible action of the present device, i.e., that of the pusher tube 56, push/pull rod 58 and cinching suture knot 23, along with the interlock pin 82, insure that the instrument 10 is used in an appropriate fashion, diminishing the potential for spillage of the excised tissue and contaminated liquids.

Attaching the cinch suture 20 to the push/pull rod 58 eliminates a separate action to close the pouch 14 which would otherwise enable misuse of the instrument 10 by allowing the rim support 76, 176, 276 to be withdrawn prior to cinching the pouch 14 closed.

It should be understood that the embodiments described herein are merely exemplary and that a person skilled in the art may make many variations and modifications without departing from the spirit and scope of the invention as defined in the appended claims.

I claim:

1. A surgical instrument, comprising:
   an elongated outer tube;
   an elongated inner rod telescopically moveable within said outer tube;
   a plurality of pouch support blades, each with a solid cross-section, at least two of said plurality of support blades attached at one end thereof to a distal end of said inner rod;
   a pouch having an open end and a closed end supported on said support blades, said support blades being accommodated in a blade channel in said pouch extending at least partially around and proximate to the periphery of said open end, said blades having a deployed configuration approximating a hoop with one of said plurality of blades overlapping a portion of a second of said plurality of blades in juxteposition.

2. The instrument of claim 1, wherein said blades have a stored configuration to permit said blades and said pouch to be inserted into said outer tube, said overlapping portion in the stored configuration having an increased length over said overlapping portion in the deployed configuration to decrease the stored length of said blades.

3. The instrument of claim 2, wherein said blades are three in number with a first blade being attached at one end to said rod and at the other end to a second blade, one end of said second blade remaining unattached and projecting toward said third blade when deployed, said third blade being attached at one end to said rod and remaining unattached at the other end and projecting towards said second blade, said second blade and said third blade overlapping at the unattached ends thereof.

4. The instrument of claim 2, wherein said blades are three in number, a first and second blade attached at one end thereof, respectively, to said rod and the other free ends thereof projecting generally in the direction of the other when deployed, and including a third blade being disposed within said channel bridging the gap between said first and second blades.

5. The instrument of claim 4, wherein said third blade is folded at the approximate middle of its length, said third blade being retained in alignment bridging said first and second blades when in said stored condition and in said deployed condition via the alignment of said fold in said blade with a fold in said pouch.

6. The instrument of claim 5, wherein said third blade is plastic and is thinned at the location of said fold.

7. The instrument of claim 2, wherein said pouch has a suture channel disposed about the periphery of said open end and a suture disposed in said suture channel, said suture being formed into a noose for constricting said open end of said pouch by a slip knot.

8. The instrument of claim 7, wherein said suture extends from said pouch, through said elongated outer tube, and attaches to said rod at a proximal end thereof, said noose tightening as said rod is telescoped out of said outer tube.

9. The instrument of claim 8, wherein said plurality of support blades are withdrawn from said blade channel when said rod is telescoped out of said outer tube.

10. The instrument of claim 9, further including a motion limiter acting upon said rod, said motion limiter permitting said rod to be telescoped out of said outer tube but disallowing said rod to be moved in the opposite direction.

11. The instrument of claim 9, further including an elongated pusher tube coaxially positioned between said outer tube and said rod, a first motion limiter attached to said pusher tube and acting upon said rod, said first motion limiter permitting said rod to be telescoped out of said pusher tube in a proximal direction but disallowing reinsertion of said rod in a distal direction, and a second motion limiter attached to said outer tube and acting upon said pusher tube, said second motion limiter permitting said pusher tube to be inserted into said outer tube but disallowing said pusher tube to be telescoped out after insertion into said outer tube.

12. The instrument of claim 11, further including means for gripping said outer tube and means for gripping said rod.

13. The instrument of claim 11, further including means for enabling and disabling the telescoping of said rod based upon the position of said pusher tube relative to said outer tube.

14. The instrument of claim 11, further including a cap attached to a distal end of said pusher tube, said cap having a first aperture therein permitting said support blades to pass therethrough and a second aperture permitting said suture to pass therethrough, said second aperture dimensioned to disallow said slip knot to pass therethrough, such that said slip knot tightens said noose as said suture is drawn through said second aperture by the movement of said rod as it telescopes out of said pusher tube.

15. The instrument of claim 13, further including means for preventing rotation of said rod relative to said pusher tube, means for preventing rotation of said pusher tube relative to said outer tube, means for visually sensing the orientation of said pouch and means for tactilely sensing the orientation of said pouch.

16. The instrument of claim 8, wherein said suture is attached to said rod by a release knot.

17. The instrument of claim 2, wherein said pouch is rolled into a tight spiral roll for storage in said outer tube in said stored configuration.

18. The instrument of claim 2, wherein said blades are two in number and are formed of superelastic metal.

19. A surgical instrument, comprising:

three elongated coaxial members, each capable of telescopic movement relative to the others;

a surgical pouch;

a plurality of pouch support blades attached to a distal end of a first of said coaxial members, said pouch support blades being accommodated in a blade channel of said surgical pouch, said blade channel extending at least partially around and proximate to the periphery of an open end of said pouch, said blades having a deployed configuration approximating a hoop with one of said plurality of blades overlapping a portion of a second of said plurality of blades, said blades having a stored configuration in which said overlapping portion is enlarged to permit said hoop to be compressed for storage without extending to its full compressed length;

said second of said coaxial members accommodating said first coaxial member within a lumen thereof, said second coaxial member having a cap on a distal end thereof with an aperture permitting said blades to extend through said cap but disallowing said pouch to pass therethrough, such that said blades and said pouch are positioned outside said second coaxial member distal to said cap in said stored and deployed state, but said blades being retractable through said cap and into the lumen of said second coaxial member when said blades are in a retracted state;

said third coaxial member accommodating said second coaxial member and said pouch within a lumen thereof when in the stored configuration, said pouch telescoping out of said third coaxial member and deploying to assume a deployed state.

20. A surgical pouch support assembly for supporting a surgical pouch at the end of an elongated element, said pouch having a peripheral support blade channel, comprising:

a plurality of flexible, arcuate blades attachable at one end of said elongated element, said blades having a deployed configuration approximating a hoop, said pouch support assembly having at least one mechanical discontinuity forming a disconnection between said blades allowing said hoop to be withdrawn from said blade channel without disturbing the integrity of said pouch, said blades overlapping in juxtaposition proximate said discontinuity to provide torsional stability to the rim.

21. A surgical instrument comprising:

an elongated outer tube;

an elongated inner rod telescopically moveable within said outer tube;

a plurality of pouch support blades attached to a distal end of said inner rod with one of said plurality of blades overlapping a portion of a second of said blades in juxtaposition;

a pouch having an open end and a closed end supported on said blades, said blades being accommodated in a blade channel In said pouch extending at least partially around and proximate to the periphery of said open end, said blades having a deployed configuration approximating a hoop, said outer tube having a closed end with at least one aperture therein, said at least one aperture permitting said blades to pass therethrough, said blades extending through said at least one aperture distally and external to said outer tube when deployed to support said pouch, said at least one aperture being dimensioned to permit said blades to slidably pass therethrough but disallow said pouch to pass therethrough such that said pouch abuts against said closed end of said outer tube and said blades slip from said blade channel, through said at least one aperture and into said outer tube when said blades are retracted therein.

22. The instrument of claim 19, wherein said aperture is offset from the radial center of said cap to facilitate accommodating said pouch within said third coaxial member when said pouch is in a rolled configuration for storage.

23. A surgical instrument, comprising:

an elongated outer tube;

an elongated inner rod telescopically moveable within said outer tube;

a plurality of pouch support blades attached to a distal end of said inner rod;

a pouch having an open end and a closed end supported on said support blades, said support blades being accommodated in a blade channel in said pouch extending at least partially around and proximate to the periphery of said open end, said blades having a deployed configuration approximating a hoop with one of said plurality of blades overlapping a portion of a second of said plurality of blades, said blades having a stored configuration to permit said blades and said pouch to be inserted into said outer tube, said pouch having a suture channel disposed about the periphery of said open end and a suture disposed in said suture channel, said suture being formed into a noose for constricting said open end of said pouch by a slip knot, said suture extending from said pouch, through said elongated outer tube, and attaching to said rod at a proximal end thereof, said noose tightening as said rod is telescoped out of said outer tube, said plurality of support blades being withdrawn from said blade channel when said rod is telescoped out of said outer tube;

an elongated pusher tube coaxially positioned between said outer tube and said rod; and a motion limiter attached to said outer tube and acting upon said pusher tube, said motion limiter permitting said pusher tube to be inserted into said outer tube but disallowing said pusher tube to be telescoped out after insertion into said outer tube.

24. The instrument of claim 23, further including means for gripping said outer tube and means for gripping said rod.

25. The instrument of claim 23, further including means for enabling and disabling the telescoping of said rod based upon the position of said pusher tube relative to said outer tube.

26. The instrument of claim 23, further including a cap attached to a distal end of said pusher tube, said cap having a first aperture therein permitting said support blades to pass therethrough and a second aperture permitting said suture to pass therethrough, said second aperture dimensioned to disallow said slip knot to pass therethrough, such that said slip knot tightens said noose as said suture is drawn through said second aperture by the movement of said rod as it telescopes out said pusher tube.

27. The instrument of claim 26, further including means for preventing rotation of said rod relative to said pusher tube, means for preventing rotation of said pusher tube relative to said outer tube, means for visually sensing the orientation of said pouch and means for tactilely sensing the orientation of said pouch.

* * * * *